United States Patent
Talbott

(10) Patent No.: US 11,723,941 B2
(45) Date of Patent: Aug. 15, 2023

(54) NUTRITIONAL SUPPLEMENTS AND METHODS OF SUPPLEMENTATION AFFECTING THE ENDOCANNABINOID SYSTEM

(71) Applicant: Amare Global, Irvine, CA (US)

(72) Inventor: Shawn M. Talbott, Draper, UT (US)

(73) Assignee: AMARE GLOBAL, Irvine, CA (US)

( * ) Notice: Subject to any disclaimer, the term of this patent is extended or adjusted under 35 U.S.C. 154(b) by 0 days.

(21) Appl. No.: 17/013,260

(22) Filed: Sep. 4, 2020

(65) Prior Publication Data

US 2021/0060111 A1 Mar. 4, 2021

Related U.S. Application Data

(60) Provisional application No. 62/895,914, filed on Sep. 4, 2019.

(51) Int. Cl.
| | | |
|---|---|---|
| A61K 36/73 | (2006.01) | |
| A61K 36/63 | (2006.01) | |
| A61K 36/324 | (2006.01) | |
| A23L 33/00 | (2016.01) | |
| A61K 36/67 | (2006.01) | |
| A23L 33/105 | (2016.01) | |
| A61K 36/23 | (2006.01) | |

(52) U.S. Cl.
CPC ............ *A61K 36/73* (2013.01); *A23L 33/105* (2016.08); *A23L 33/30* (2016.08); *A61K 36/23* (2013.01); *A61K 36/324* (2013.01); *A61K 36/63* (2013.01); *A61K 36/67* (2013.01)

(58) Field of Classification Search
None
See application file for complete search history.

(56) References Cited

U.S. PATENT DOCUMENTS

| | | |
|---|---|---|
| 7,781,572 B2 | 8/2010 | Bartlett et al. |
| 7,794,761 B2 | 9/2010 | Shelby et al. |
| 9,028,890 B2 | 5/2015 | Ferrari et al. |
| 9,700,071 B2 | 7/2017 | Silver et al. |
| 10,213,471 B1 * | 2/2019 | Buckner ............... A61K 33/14 |
| 10,449,148 B2 | 10/2019 | Gutierrez et al. |
| 2003/0206972 A1 | 11/2003 | Babish et al. |
| 2007/0269541 A1 | 11/2007 | Rohdewald |
| 2009/0148433 A1 | 6/2009 | Naidu et al. |
| 2011/0206649 A1 | 8/2011 | Bergonzelli et al. |
| 2011/0262618 A1 | 10/2011 | Melwitz |
| 2013/0064803 A1 | 3/2013 | Naidu et al. |
| 2013/0261183 A1 | 10/2013 | Bhagat |
| 2016/0000854 A1 | 1/2016 | Osborne et al. |
| 2019/0183849 A1 * | 6/2019 | Kariman ................. A61P 25/02 |
| 2020/0297605 A1 | 9/2020 | Ambrogio et al. |
| 2020/0352206 A1 | 11/2020 | Wagner-Salvini |
| 2020/0397711 A1 | 12/2020 | Lee |
| 2021/0069280 A1 | 3/2021 | Talbott |
| 2021/0121490 A1 | 4/2021 | Takahashi et al. |

FOREIGN PATENT DOCUMENTS

| | | |
|---|---|---|
| CN | 106615516 A | 5/2017 |
| WO | 03/21515 A2 | 3/2003 |
| WO | 2014/083438 A2 | 6/2014 |
| WO | 2015/006646 A1 | 1/2015 |
| WO | 2015/153841 A1 | 10/2015 |
| WO | 2018/013871 A1 | 1/2018 |
| WO | 2018/027070 A1 | 2/2018 |
| WO | 2018/035212 A1 | 2/2018 |
| WO | 2018/195097 A1 | 10/2018 |
| WO | 2019/056129 A2 | 3/2019 |
| WO | 2019/069096 A1 | 4/2019 |
| WO | 2019/078005 A1 | 4/2019 |
| WO | 2019/090273 A2 | 5/2019 |

OTHER PUBLICATIONS

Kapoor et al. (2009) J. Agric. Food Chem. 57: 5358-5364. (Year: 2009).*
Kiralan et al. (2014) Industrial Crops and Products 57: 52-58. (Year: 2014).*
Lotterodt et al. (2010) LWT—Food Science and Technology 43: 1409-1413. (Year: 2010).*
Raskin et al. (2004) Current Pharmaceutical Design, 10: 3419-3429. (Year: 2004).*
Revilla et al. (1998) J. Agric. Food Chem. 46: 4592-4597. (Year: 1998).*
Kristin Schmidt, Philip J. Cowen, Catherine J. Harmer, George Tzortzis, Steven Errington, Philip W. J. Burnet, Prebiotic intake reduces the waking cortisol response and alters emotional bias in healthy volunteers, 2015, Psychopharmacology, vol. 232, pp. 1793-1801 (Year: 2015).
L.M. Foster, T.A. Tompkins and W.J. Dahl, A comprehensive post-market review of studies on a probiotic product containing *Lactobacillus helveticus* R0052 and *Lactobacillus rhamnosus* R0011, 2011, Beneficial Microbes, vol. 2, Issue 4, pp. 319-334 (Year: 2011).
Michael Messaoudi et al., Beneficial psychological effects of a probiotic formulation (*Lactobacillus helveticus* R0052 and *Bifidobacterium longum* R0175) in healthy human volunteers, 2011, Gut Microbes, vol. 2, No. 4, pp. 256-261 (Year: 2011).
"International Search Report and Written Opinion of the International Searching Authority," issued in connection with Int'l Appl. No. PCT/US18/48945, dated Nov. 21, 2018 (7 pages).

(Continued)

*Primary Examiner* — Russell G Fiebig

(74) *Attorney, Agent, or Firm* — Holland & Hart LLP

(57) ABSTRACT

Nutritional supplements and methods of nutritional supplementation affecting the endocannabinoid system are provided. These nutritional supplements and methods of nutritional supplementation support the endocannabinoid systems of subjects by providing a blend of hemp oil, black pepper oil, black cumin seed oil, and white frankincense oil to prime ECS receptors and activate them to provide improvements to the ECS in a subject, affecting their pain response, mood, stress response, and sleep.

1 Claim, No Drawings

(56) References Cited

OTHER PUBLICATIONS

"International Search Report and Written Opinion of the International Searching Authority," issued in connection with Int'l Appl. No. PCT/US18/48980, dated Nov. 30, 2018 (7 pages).
"International Search Report and Written Opinion of the International Searching Authority," issued in connection with Int'l Appl. No. PCT/US20/49469 dated Dec. 10, 2020 (8 pages).
"International Search Report and Written Opinion of the International Searching Authority," issued in connection with Int'l Appl. No. PCT/US20/49545, dated Dec. 10, 2020 (14 pages).
"International Search Report and Written Opinion of the International Searching Authority," issued in connection with Int'l Appl. No. PCT/US20/49555, dated Dec. 21, 2020 (13 pages).
"International Search Report and Written Opinion of the International Searching Authority," issued in connection with Int'l Appl. No. PCT/US20/49560, dated Jan. 7, 2021 (8 pages).
Amare Global, product names Sleep+, p. 2, Key Ingredients, Clinical Study at 2013, https://www.amare.com/corporate/SleepPlus, 1 page; retrieved Feb. 21, 2020.
Ambati, R. et al. Astaxanthin: Sources, Extraction, Stability, Biological Activities and its Commercial Applications—A Review. Marine Drugs 12:128-152, 2014. (Year: 2014).
Frotela-Saseta et al. (2011) Phytother. Res. 25: 1870-1875. (Year: 2011).
Ji, X. et al. Astaxanthin Improves Cognitive Performance in Mice . . . Brain Research 1659:88-95, 2017. (Year: 2017).
Jiang, T. Health Benefits of Culinary Herbs and Spices J of AOAC Int 102(2)395-411 Mar./Apr. 2019. (Year: 2019).
Kaur et al. (2008) Nutr. Cancer 60(Suppl. 1): 2-11. (Year: 2008).
Ku et al. (2008) Wood Sci. Technol. 42; 47-60. (Year: 2008).
Lizarraga et al. (2007) FEBS Journal 274: 4802-4811. (Year: 2007).
McGann et al. (2007) Food and Chemical Toxicology 45: 1224-1230. (Year: 2007).
Nature's Plus, Ageless Mood Support, title, p. 1, Supplement Facts, Apr. 27, 2015, https://www.amazaon.com/Natrues-Plus-Ageloss-Mood-Support/dp/B00CELG1XI; r1 page, retrieved Feb. 21, 2020.
Radhakrishnan et al. (2011) Frontiers in Bioscience E3, 1509-1523. (Year: 2011).
Reagan-Shaw et al. (2010) Nutrition and Cancer 62(4): 517-524. (Year: 2010).
Rohdewald (2002) Intern. J. Clin. Pharmacol. Ther. vol. 40, No. 4: (158-168). (Year: 2002).
Schauss A. Advances in the Study of the Health Benefits and Mechanisms of Action of the Pulp and Seed of the Amazonian Palm Fruit, Euterpe oleracea Mart. Known as Acai. Chapter 10 of Fruits, Vegetables and Herbs, 2016. (Year: 2016).
Sorndech, W. et al. Isomalto-Oligosaccharides: Recent Insights in Production Technology and Their Use for Food and Medical Applications. Food Science and Technology 95:135-142, 2018. (Year: 2018).
Speranza et al., "Astaxanthin Treatment Reduced Oxidative Induced Pro-Inflammatory Cytokines Secretion in U937: SHP-1 as a Novel Biological Target", Marine Drugs, vol. 20, Issue 4, Apr. 2012, pp. 890-899.
Sreedhar A. et al. Next-Gen Therapeutics for Skin Cancer: Nutraceuticals Nutrition and Cancer 70(5)697-709 Jul. 2019. (Year: 2019).
Talbott et al. "Effect of coordinated probiotic/prebiotic/phytobiotic supplementation on microbiome balance and psychological mood state in healthy stressed adults" Functional Foods in Health and Disease, Apr. 30, 2019; 9(4):265-275.
Talbott, S. et al. "Effect of Monocot Grass Extract on mood state and sleep patterns in moderately stress subjects", J Int Soc Sports Nutr. 2013, 10 (Suppl 1): p. 26. (Year: 2013).
University of Wisconsin School of Medicine and Health (Non-Pharmaceutical Approaches for Depression Towards Vitality, Pearls for Clinicians, Mar. 12, 2007) (Year: 2007).
Veeriah et al. (2006) Molecular Carcinogenesis 45:164-174. (Year: 2006).
Yamashita, E. Let Astaxanthin Be Thy Medicine PharmaNutrition 3:115-122, 2015. (Year: 2015).

* cited by examiner

NUTRITIONAL SUPPLEMENTS AND METHODS OF SUPPLEMENTATION AFFECTING THE ENDOCANNABINOID SYSTEM

BACKGROUND

The following relates generally to nutritional supplements and methods of nutritional supplementation of subjects. More specifically the following relates to nutritional supplements and methods of supplementation affecting the endocannabinoid system. These nutritional supplements and methods of nutritional supplementation support endocannabinoid systems of subjects to improve their pain, mood, stress and sleep.

The endocannabinoid system ("ECS") is becoming the target of significant attention in recent years, having been recently associated with modulatory activity in the brain, and in the endocrine and immune systems. The system includes two primary endocannabinoid receptors, CB1 and CB2, which are found primarily in the nervous system and brain tissues.

The ECS is, as yet, poorly understood, and as such, its roles are still becoming more clearly understood. It is, however, thought to play a role in many bodily functions and systems, including pain response, mood, stress response, and sleep.

Because little is known about regulation of this system, few options are known for supporting/regulating the ECS and assuring its function and strength. There is thus a need for nutritional supplements and methods of nutritional supplementation for supporting/regulating the ECS in a subject. In some instances, there is a need for nutritional supplements and methods of nutritional supplementation which may allow improvements to the ECS in a subject, improving their pain response, mood, stress response, and sleep.

SUMMARY

Improved nutritional supplements and methods of nutritional supplementation are described to support the endocannabinoid system of an individual. Generally, the described unique nutritional supplements and methods of nutritional supplementation improve pain, mood, stress and/or sleep in a subject.

In some aspects, methods for ECS system support are provided which include administering to the subject an effective amount of a composition comprising hemp oil, black pepper oil, black cumin seed oil, and white frankincense oil. In some aspects, the hemp oil is full spectrum hemp oil.

In some methods, the compositions may include between about 15 mg and about 50 mg of hemp oil. In others, the compositions may include between about 25 mg and about 40 mg of hemp oil. In still others, the compositions may include about 36 mg of hemp oil.

In some methods, the compositions may include between about 5 mg and about 50 mg of black pepper oil. In others, the compositions may include between about 10 mg and about 30 mg of black pepper oil. In still others, the compositions may include about 15 mg of black pepper oil.

In some methods, the compositions may include between about 1 mg and about 20 mg black cumin seed oil. In others, the compositions may include between about 3 mg and about 10 mg black cumin seed oil. In still others, the compositions may include about 6 mg of black cumin seed oil.

In some methods, the composition may include between about 0.5 mg and about 5 mg white frankincense oil. In others, the compositions may include between about 1 mg and about 3 mg white frankincense oil. In still others, the compositions may include about 2 mg of white frankincense oil.

Some methods described herein further include supplements including olive oil. In some methods, the olive oil is extra virgin olive oil. In some methods, the compositions may include between about 800 mg and about 900 mg olive oil. In others, the compositions may include between about 830 mg and about 880 mg olive oil. In still others, the compositions may include about 857 mg of olive oil.

The described methods may further include the step of identifying a subject in need of improvement of pain, mood, stress and/or sleep.

In some aspects, methods of improving pain, mood, stress and/or sleep in a subject are described which include administering to the subject an effective amount of a composition comprising full spectrum hemp oil standardized to 20 mg CBD, black pepper oil standardized to 6 mg b-caryophyllene, black cumin seed oil standardized to 3% thymoquinone, and white frankincense oil.

In some aspects, the compositions include between about 15 mg to about 50 mg of hemp oil. In others, compositions include between about 25 mg to about 40 mg of hemp oil. In still others, the compositions include about 36 mg of hemp oil.

In some methods, the compositions may include between about 5 mg and about 50 mg of black pepper oil. In others, the compositions may include between about 10 mg and about 30 mg of black pepper oil. In still others, the compositions may include about 15 mg of black pepper oil.

In some methods, the compositions may include between about 1 mg and about 20 mg black cumin seed oil. In others, the compositions may include between about 3 mg and about 10 mg black cumin seed oil. In still others, the compositions may include about 6 mg of black cumin seed oil.

In some methods, the composition may include between about 0.5 mg and about 5 mg white frankincense oil. In others, the compositions may include between about 1 mg and about 3 mg white frankincense oil. In still others, the compositions may include about 2 mg of white frankincense oil.

Some methods described herein further include supplements including olive oil. In some methods, the olive oil is extra virgin olive oil. In some methods, the compositions may include between about 800 mg and about 900 mg olive oil. In others, the compositions may include between about 830 mg and about 880 mg olive oil. In still others, the compositions may include about 857 mg of olive oil.

The described methods may further include the step of identifying a subject in need of improvement of pain, mood, stress and/or sleep.

Methods of improving pain, mood, stress and/or sleep in a subject by supporting the ECS are described, which include administering to the subject an effective amount of a composition comprising approximately 36 mg of full spectrum hemp oil standardized to 20 mg CBD, approximately 15 mg of black pepper oil standardized to 6 mg b-caryophyllene, approximately 6 mg of black cumin seed oil standardized to 3% thymoquinone, approximately 2 mg of white frankincense oil, and approximately 857 mg olive oil.

Such methods may further include the step of identifying a subject in need of improvement of pain, mood, stress and/or sleep.

Nutritional supplements are also described, the supplements including a composition including hemp oil, black pepper oil, black cumin seed oil, and white frankincense oil.

In some such supplements, the compositions may include hemp oil which is full spectrum hemp oil. In others, the compositions may include between about 15 mg to about 50 mg of hemp oil. In others, the compositions may include between about 25 mg to about 40 mg of hemp oil. In still others, the compositions may include about 36 mg of hemp oil.

In some supplements, the compositions may include between about 5 mg and about 50 mg of black pepper oil. In others, the compositions may include between about 10 mg and about 30 mg of black pepper oil. In still others, the compositions may include about 15 mg of black pepper oil.

In some methods, the compositions may include between about 1 mg and about 20 mg black cumin seed oil. In others, the compositions may include between about 3 mg and about 10 mg black cumin seed oil. In still others, the compositions may include about 6 mg of black cumin seed oil.

In some methods, the composition may include between about 0.5 mg and about 5 mg white frankincense oil. In others, the compositions may include between about 1 mg and about 3 mg white frankincense oil. In still others, the compositions may include about 2 mg of white frankincense oil.

Some methods described herein further include supplements including olive oil. In some methods, the olive oil is extra virgin olive oil. In some methods, the compositions may include between about 800 mg and about 900 mg olive oil. In others, the compositions may include between about 830 mg and about 880 mg olive oil. In still others, the compositions may include about 857 mg of olive oil.

Nutritional supplements are also described, the supplements including a composition including full spectrum hemp oil standardized to 20 mg CBD, black pepper oil standardized to 6 mg b-caryophyllene, black cumin seed oil standardized to 3% thymoquinone, and white frankincense oil.

In some such supplements, the compositions may include between about 15 mg to about 50 mg of hemp oil. In others, the compositions may include between about 25 mg to about 40 mg of hemp oil. In still others, the compositions may include about 36 mg of hemp oil.

In some methods, the compositions may include between about 5 mg and about 50 mg of black pepper oil. In others, the compositions may include between about 10 mg and about 30 mg of black pepper oil. In still others, the compositions may include about 15 mg of black pepper oil.

In some methods, the compositions may include between about 1 mg and about 20 mg black cumin seed oil. In others, the compositions may include between about 3 mg and about 10 mg black cumin seed oil. In still others, the compositions may include about 6 mg of black cumin seed oil.

In some methods, the composition may include between about 0.5 mg and about 5 mg white frankincense oil. In others, the compositions may include between about 1 mg and about 3 mg white frankincense oil. In still others, the compositions may include about 2 mg of white frankincense oil.

Some methods described herein further include supplements including olive oil. In some methods, the olive oil is extra virgin olive oil. In some methods, the compositions may include between about 800 mg and about 900 mg olive oil. In others, the compositions may include between about 830 mg and about 880 mg olive oil. In still others, the compositions may include about 857 mg of olive oil.

Nutritional supplements are also described which include approximately 36 mg of full spectrum hemp oil standardized to 20 mg CBD, approximately 15 mg of black pepper oil standardized to 6 mg b-caryophyllene, approximately 6 mg of black cumin seed oil standardized to 3% thymoquinone, approximately 2 mg of white frankincense oil, and approximately 857 mg olive oil.

DETAILED DESCRIPTION

As used herein, treatment means any manner in which the symptoms or pathology of a condition, disorder or disease are ameliorated or otherwise beneficially altered. Treatment also encompasses any pharmaceutical use of the compositions herein.

The supplement compositions of the present disclosure may be administered in a variety of suitable dosage forms, including, without limitation, tablets, capsules, granules, powders, liquids, liposome inclusions, ointments, gels, external powders, sprays, inhalable powders, injectable preparations (solutions, suspensions, emulsions, solids to be dissolved when used, etc.), eye drops, eye ointments, suppositories, and the like can be selected appropriately depending on the administration method, and the compositions of the present disclosure can be accordingly formulated. Formulation in general is described in references including Comprehensive Medicinal Chemistry, Volume 5, Editor Hansch et al, Pergamon Press 1990.

As used herein, any range set forth is inclusive of the end points of the range unless otherwise stated.

As used herein, "effective amount" refers to an amount of a substance which is sufficient to achieve its intended purpose or effect. Various biological factors may affect the ability of a delivered substance to perform its intended task. Therefore, an "effective amount" may be dependent on such biological factors. An effective amount of a compound for treating a disorder is an amount that is sufficient to ameliorate, or in some manner reduce a symptom or stop or reverse progression of a condition. Such amount may be administered as a single dosage or may be administered according to a regimen whereby it is effective. The achievement of therapeutic effects may be measured by a physician or other qualified medical personnel using evaluations known in the art, (for example with testosterone supplementation therapy, physical examination, blood and saliva tests may be used), it is recognized that individual variation and response to treatments may make the achievement of therapeutic effects a subjective decision.

Further, determination of the effectiveness of the amount is well within the knowledge and ability of one of ordinary skill in the art.

As used herein, "administration," and "administering" may be used interchangeably, and refer to the act of presenting, applying, or introducing a drug to a subject in order to achieve a desired physiological or psychological response.

As used herein, amelioration of the symptoms of a particular disorder by administration of a particular pharmaceutical composition refers to any lessening, whether permanent or temporary, lasting or transient that can be attributed to or associated with administration of the composition.

Many individuals struggle with pain, low moods, poor management or strong responses to stress and low-quality sleep. The present disclosure provides nutritional supplements and methods of nutritional supplementation to support the ECS of an individual, and thus to support improvements in pain, mood, stress and sleep.

Without being limited to any one theory, it is understood that the supplements and methods of supplementation disclosed herein act using a previously-unknown mechanism of first priming the ECS receptors, and then activating them, providing benefits superior to currently available solutions.

In some embodiments, the use of full-spectrum hemp oil provides a range of 100+ naturally-occurring phytocannabinoids, instead of delivering a single cannabinoid, as is done in many other available supplements. This may result in synergistic effects not elicited by administration of a single cannabinoid compound such as CBD. It is further believed that phytocannabinoids preferentially bind to the CB1 receptor, especially those found in the brain areas of the ECS, affecting reactions to stress, anxiety, mood, pain and sleep.

The supplements and methods of supplementation described in the present disclosure further provide black pepper oil comprising terpenes which bind preferentially to the CB2 receptors of the ECS, synergistically easing pain and inflammation in a subject receiving the compositions of this disclosure.

Lastly, the nutritional supplements and methods of nutritional supplementation disclosed further provide polyphenols from white frankincense oil and quinones from black cumin seed oil. Without being limited to any one theory, these polyphenols and quinones act together and/or separately to prime the full range of CB1 and CB2 receptors to prepare them to receive and bind the hemp phytocannabinoids provided by the supplements of this disclosure.

By priming the ECS while administering a full-spectrum hemp oil as a source of phytocannabinoids, the nutritional supplements and methods of supplementation of the present disclosure provide a superior and unexpectedly complete priming and activation of the ECS, resulting in superior effects on the stress response, pain, mood/anxiety and sleep of a subject.

It should be noted that the methods described herein describe possible implementations, and that the operations and the steps may be rearranged or otherwise modified and that other implementations are possible. Further, aspects from two or more of the methods may be combined.

As used herein, including in the claims, "or" as used in a list of items (e.g., a list of items prefaced by a phrase such as "at least one of" or "one or more of") indicates an inclusive list such that, for example, a list of at least one of A, B, or C means A or B or C or AB or AC or BC or ABC (i.e., A and B and C). Also, as used herein, the phrase "based on" shall not be construed as a reference to a closed set of conditions. For example, an exemplary step that is described as "based on condition A" may be based on both a condition A and a condition B without departing from the scope of the present disclosure. In other words, as used herein, the phrase "based on" shall be construed in the same manner as the phrase "based at least in part on."

In the appended figures, similar components or features may have the same reference label. Further, various components of the same type may be distinguished by following the reference label by a dash and a second label that distinguishes among the similar components. If just the first reference label is used in the specification, the description is applicable to any one of the similar components having the same first reference label irrespective of the second reference label, or other subsequent reference label.

The description set forth herein, in connection with the appended drawings, describes example configurations and does not represent all the examples that may be implemented or that are within the scope of the claims. The term "exemplary" used herein means "serving as an example, instance, or illustration," and not "preferred" or "advantageous over other examples." The detailed description includes specific details for the purpose of providing an understanding of the described techniques. These techniques, however, may be practiced without these specific details. In some instances, well-known structures and devices are shown in block diagram form in order to avoid obscuring the concepts of the described examples.

The description herein is provided to enable a person skilled in the art to make or use the disclosure. Various modifications to the disclosure will be readily apparent to those skilled in the art, and the generic principles defined herein may be applied to other variations without departing from the scope of the disclosure. Thus, the disclosure is not limited to the examples and designs described herein, but is to be accorded the broadest scope consistent with the principles and novel features disclosed herein.

What is claimed is:

1. A method of administering a nutritional supplement to a subject, comprising:
   identifying that the subject is in need of improvement of mood; and
   administering the nutritional supplement to the subject, wherein the nutritional supplement is a composition that comprises:
   between about 15 mg to about 50 mg full spectrum hemp oil;
   between about 5 mg and about 50 mg black pepper oil, which comprises b-caryophyllene;
   between about 1 mg and about 20 mg black cumin seed oil, which comprises thymoquinone;
   between about .5 mg and about 5 mg white frankincense oil; and
   between about 800 mg and about 900 mg olive oil.

* * * * *